United States Patent [19]

Rondeau et al.

[11] Patent Number: 5,879,412
[45] Date of Patent: Mar. 9, 1999

[54] COMPOSITIONS AND PROCESSES FOR DYEING KERATIN FIBERS WITH AN OXIDATION BASE, A COUPLER, A CATIONIC DIRECT DYE, AND AN OXIDIZING AGENT

[75] Inventors: Christine Rondeau, Sartrouville; Jean Cotteret, Verneuil sur Seine; Roland de la Mettrie, Le Vesinet, all of France

[73] Assignee: L'Oreal, Paris, France

[21] Appl. No.: 994,446

[22] Filed: Dec. 19, 1997

[30] Foreign Application Priority Data

Dec. 23, 1996 [FR] France .................................. 96 15894

[51] Int. Cl.$^6$ ...................................................... A61K 7/13
[52] U.S. Cl. .......................... 8/411; 8/407; 8/408; 8/409; 8/410; 8/423; 8/426
[58] Field of Search ............................... 8/405, 406, 407, 8/408, 409, 410, 411, 423, 426

[56] References Cited

U.S. PATENT DOCUMENTS

| | | | |
|---|---|---|---|
| 3,524,842 | 8/1970 | Grossman et al. | 8/426 |
| 3,578,386 | 5/1971 | Kalopissis et al. | 8/426 |
| 3,869,454 | 3/1975 | Lang et al. | 534/778 |
| 3,985,499 | 10/1976 | Lang et al. | 8/426 |
| 4,025,301 | 5/1977 | Lang et al. | 8/426 |
| 4,425,132 | 1/1984 | Grollier et al. | 8/405 |
| 4,865,619 | 9/1989 | Junino et al. | 8/410 |
| 5,637,115 | 6/1997 | Balzer et al. | 8/407 |

FOREIGN PATENT DOCUMENTS

| | | |
|---|---|---|
| 0 739 622 | 10/1996 | European Pat. Off. . |
| 2 615 732 | 12/1988 | France . |
| 1 211 801 | 11/1970 | United Kingdom . |
| 2 180 215 | 3/1987 | United Kingdom . |
| WO 95/15144 | 6/1995 | WIPO . |

*Primary Examiner*—Paul Lieberman
*Assistant Examiner*—Caroline D. Liott
*Attorney, Agent, or Firm*—Finnegan, Henderson, Farabow, Garrett & Dunner, L.L.P.

[57] ABSTRACT

A ready-to-use composition for the oxidation dyeing of keratin fibers, in particular human keratin fibers such as hair, this composition comprising at least one oxidation base selected from para-phenylenediamines and bis(phenyl)-alkylenediamines, in combination with at least one coupler selected from meta-phenylenediamines, at least one selected cationic direct dye and at least one oxidizing agent, as well as to the dyeing process using this composition.

33 Claims, No Drawings

COMPOSITIONS AND PROCESSES FOR DYEING KERATIN FIBERS WITH AN OXIDATION BASE, A COUPLER, A CATIONIC DIRECT DYE, AND AN OXIDIZING AGENT

The technology involved in this application is related to that disclosed in the following co-pending U.S. applications filed on even date herewith:

U.S. Ser. No. 08/994,127, U.S. Ser. No. 08/994,130 and U.S. Ser. No. 08/994,444.

The specifications of these related applications are hereby specifically incorporated by reference.

The present invention relates to a ready-to-use composition for the oxidation dyeing of keratin fibers, in particular human keratin fibers such as the hair, this composition comprising, in a medium which is suitable for dyeing, at least one oxidation base selected from para-phenylenediamines and bis(phenyl)-alkylenediamines, in combination with at least one coupler selected from meta-phenylenediamines, at least one selected cationic direct dye and at least one oxidizing agent, as well as to the dyeing process using this composition. The invention also relates to a dyeing kit for the preparation of such a ready-to-use composition.

It is known to dye keratin fibers, and in particular human hair, with dye compositions containing oxidation dye precursors, in particular ortho- or para-phenylenediamines, and ortho- or para-aminophenols, which are generally referred to as oxidation bases. Oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or color modifiers, the latter being selected in particular from aromatic meta-diamines, meta-aminophenols, meta-phenylenediamines and certain heterocyclic compounds.

The variety of compounds used as regards the oxidation bases and the couplers allows a wide range of colors to be obtained.

It is also known that in order to vary the shades obtained further and to give them glints, it is possible to use, in combination with the oxidation dye precursors and the couplers, direct dyes, i.e., colored substances which provide coloration in the absence of an oxidizing agent.

The so-called "permanent" coloration obtained by means of these oxidation dyes must moreover satisfy a certain number of requirements. Thus, it must be able to give shades of the desired intensity and it must be able to withstand external agents (light, bad weather, washing, permanent waving, perspiration, rubbing).

The great majority of direct dyes belong to the family of nitrobenzene compounds and have the drawback, when they are incorporated into dye compositions, of leading to colorations that have insufficient endurance, i.e., fastness, in particular with respect to shampooing.

The present invention is aimed at proposing novel compositions for the oxidation dyeing of keratin fibers, and in particular human keratin fibers such as the hair, which make it possible to obtain radiant colorations that are rich in glints while at the same time with good endurance properties, in particular.

The inventors have discovered that it is possible to obtain novel dyes that are both radiant and have good endurance by combining:

at least one oxidation base selected from para-phenylenediamines and bis(phenyl)alkylenediamines, and the acid-addition salts thereof, at least one coupler selected from meta-phenylenediamines, and the acid-addition salts thereof, at least one cationic direct dye of formula I below, and at least one oxidizing agent.

The first subject of the invention is thus a ready-to-use composition for the oxidation dyeing of keratin fibers, and in particular human keratin fibers such as the hair, characterized in that it comprises, in a medium which is suitable for dyeing:

at least one oxidation base selected from para-phenylenediamines and bis(phenyl)alkylenediamines, and the acid-addition salts thereof, at least one coupler selected from meta-phenylenediamines, and the acid-addition salts thereof, at least one cationic direct dye selected from the compounds of formula (I) below:

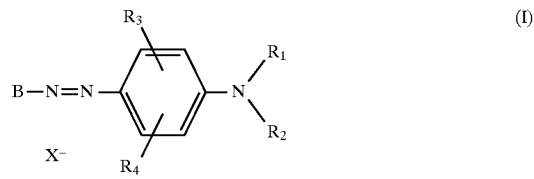

in which:

$R_1$ represents a hydrogen atom or a $C_1$–$C_4$ alkyl radical, $R_2$ represents a hydrogen atom, an alkyl radical which may be substituted with a —CN radical or with an amino group, a 4'-aminophenyl radical or forms, with $R_1$ or with a carbon atom of the benzene ring supporting the radicals $R_3$ and $R_4$, an optionally oxygenated and/or nitrogenous heterocycle which may be substituted with a $C_1$–$C_4$ alkyl radical, $R_3$ and $R_4$ each independently represent a hydrogen atom, a halogen atom such as bromine, chlorine, iodine or fluorine, a $C_1$–$C_4$ alkyl or $C_1$–$C_4$ alkoxy radical or a —CN radical, $X^-$ represents an anion preferably selected from chloride, methylsulphate and acetate, B represents a group selected from the structures B1 to B11 below:

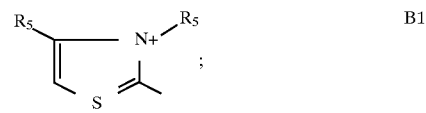

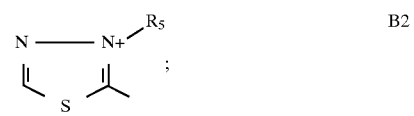

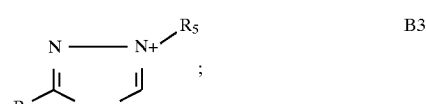

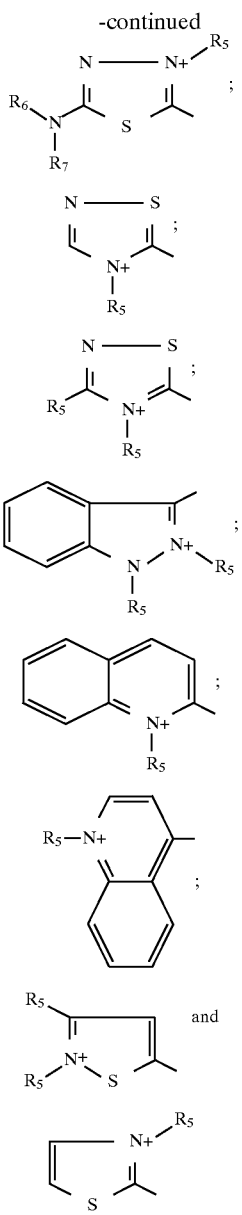

-continued

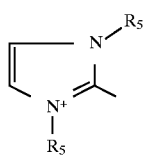

in which:

R$_5$ represents a C$_1$–C$_4$ alkyl radical,

R$_6$ and R$_7$ each independently represent a hydrogen atom or a C$_1$–C$_4$ alkyl radical;

wherein when R$_1$ and R$_2$ form a nitrogenous heterocycle, or when R$_3$ and R$_4$ represent a C$_1$–C$_4$ alkyl radical or a C$_1$–C$_4$ alkoxy radical, or when R$_2$ represents a 4'-aminophenyl radical, then B can also represent a group of structure B12 below:

B$^{12}$ in which R$_5$ has the same meaning as that indicated above for the structures B1 to B11; and at least one oxidizing agent.

The ready-to-use dye compositions in accordance with the invention make it possible to obtain colorations in ash or golden natural shades which effectively withstand the various treatments to which the hair may be subjected and in particular with regard to shampoos.

A subject of the invention is also a process for the oxidation dyeing of keratin fibers using this ready-to-use dye composition.

The para-phenylenediamines which can be used as oxidation bases in ready-to-use dye compositions in accordance with the invention are preferably selected from the compounds of formula (II) below, and the acid-addition salts thereof:

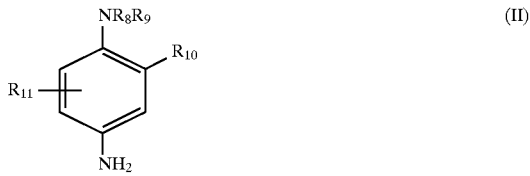

(II)

in which:

R$_8$ represents a hydrogen atom, a C$_1$–C$_4$ alkyl, C$_1$–C$_4$ monohydroxyalkyl, C$_2$–C$_4$ polyhydroxyalkyl, phenyl, 4'-aminophenyl or (C$_1$–C$_4$)alkoxy(C$_1$–C$_4$)alkyl radical, R$_9$ represents a hydrogen atom or a C$_1$–C$_4$ alkyl, C$_1$–C$_4$ monohydroxyalkyl or C$_2$–C$_4$ polyhydroxyalkyl radical, R$_{10}$ represents a hydrogen atom, a halogen atom such as a chlorine, bromine, iodine or fluorine atom, or a C$_1$–C$_4$ alkyl, C$_1$–C$_4$ monohydroxyalkyl, C$_1$–C$_4$ hydroxyalkoxy, C$_1$–C$_4$ mesylaminoalkoxy, C$_1$–C$_4$ carbamoylaminoalkoxy or C$_1$–C$_4$ acetylaminoalkoxy radical, R$_{11}$ represents a hydrogen atom or a C$_1$–C$_4$ alkyl radical.

Among the para-phenylenediamines of formula (II) above, mention may be made more particularly of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine and 2-β-acetylaminoethyloxy-para-phenylenediamine, and the acid-addition salts thereof.

Among the para-phenylenediamines of formula (II) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the acid-addition salts thereof are most particularly preferred.

The bis(phenyl)alkylenediamines which can be used as oxidation base in the ready-to-use dye compositions in accordance with the invention are preferably selected from the compounds of formula (III) below, and the acid-addition salts thereof:

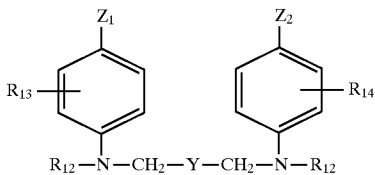

in which:

$Z_1$ and $Z_2$ each independently represents a hydroxyl radical or $NHR_{15}$ in which $R_{15}$ represents a hydrogen atom or a $C_1$–$C_4$ alkyl radical, $R_{12}$ represents a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino residue can be substituted, $R_{13}$ and $R_{14}$ each independently represents a hydrogen or halogen atom or a $C_1$–$C_4$ alkyl radical, Y represents a radical selected from the following radicals:
—$(CH_2)_n$—; —$(CH_2)_m$—O—$(CH_2)_m$—; —$(CH_2)$m—CHOH—$(CH_2)_m$— and

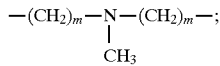

in which:

n is an integer ranging from 0 to 8 and m is an integer ranging from 0 to 4.

Among the bis(phenyl)alkylenediamines of formula (III) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the acid-addition salts thereof.

Among these bis(phenyl)alkylenediamines of formula (III), N,N'-bis(β-hydroxyethyl)-N,N'-bis(4'aminophenyl)-1,3-diaminopropanol or one of the acid-addition salts thereof is particularly preferred.

The meta-phenylenediamines which can be used as couplers in the ready-to-use dye compositions in accordance with the invention are preferably selected from the compounds of formula (IV) below, and the acid-addition salts thereof:

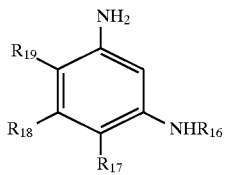

in which:

$R_{16}$ represents a hydrogen atom or a $C_1$–$C_4$ alkyl, $C_1$–$C_4$ monohydroxyalkyl or $C_2$–$C_4$ polyhydroxyalkyl radical;

$R_{17}$ and $R_{18}$ each independently represents a hydrogen atom or a $C_1$–$C_4$ alkyl, $C_1$–$C_4$ monohydroxyalkoxy or $C_2$–$C_4$ polyhydroxyalkoxy radical;

$R_{19}$ represents a hydrogen atom, a $C_1$–$C_4$ alkoxy, $C_1$–$C_4$ aminoalkoxy, $C_1$–$C_4$ monohydroxyalkoxy or $C_2$–$C_4$ polyhydroxyalkoxy radical or a 2,4-diaminophenoxyalkoxy radical.

Among the meta-phenylenediamines of formula (IV) above, mention may be made more particularly of meta-phenylenediamine, 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene and 2-amino4-N-(β-hydroxyethyl)amino-1-methoxybenzene, and the acid-addition salts thereof.

The acid-addition salts which can be used in the context of the dye compositions of the invention are selected in particular from the hydrochlorides, hydrobromides, sulphates and tartrates.

The cationic direct dyes of formula (I) which can be used in the ready-to-use dye compositions in accordance with the invention are known compounds and are described, for example, in patent applications WO 95/01772,, WO 95/15144 and EP-A-0 714 954, the disclosures of which are specifically incorporated by reference herein.

Among the cationic direct dyes of formula (I) which can be used in the ready-to-use dye compositions in accordance with the invention, mention may be made more particularly of the compounds corresponding to structures (I1) to (I26) below:

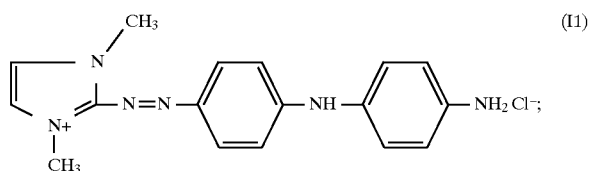

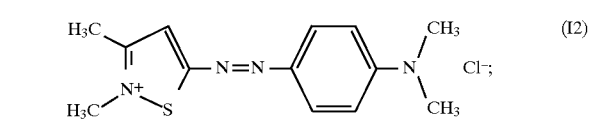

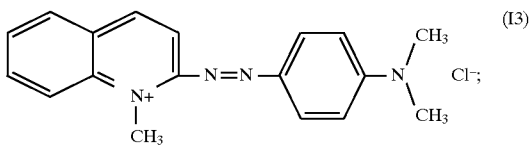

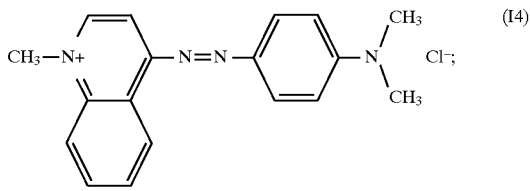

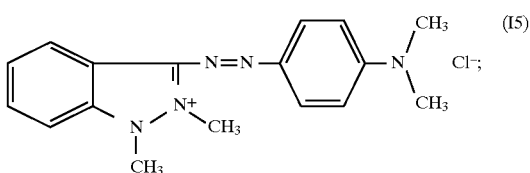

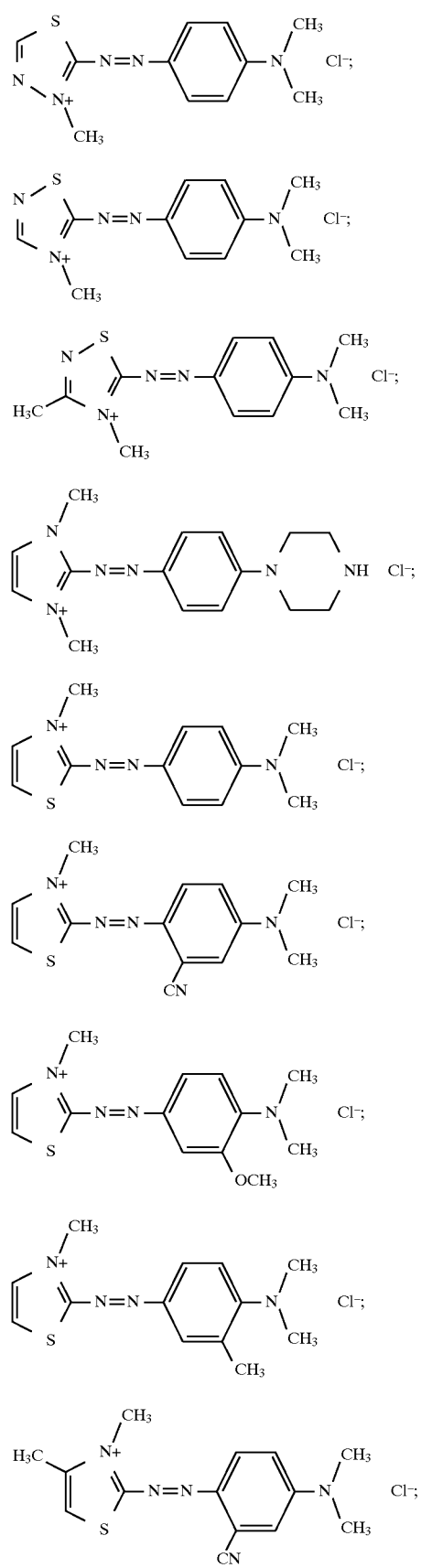
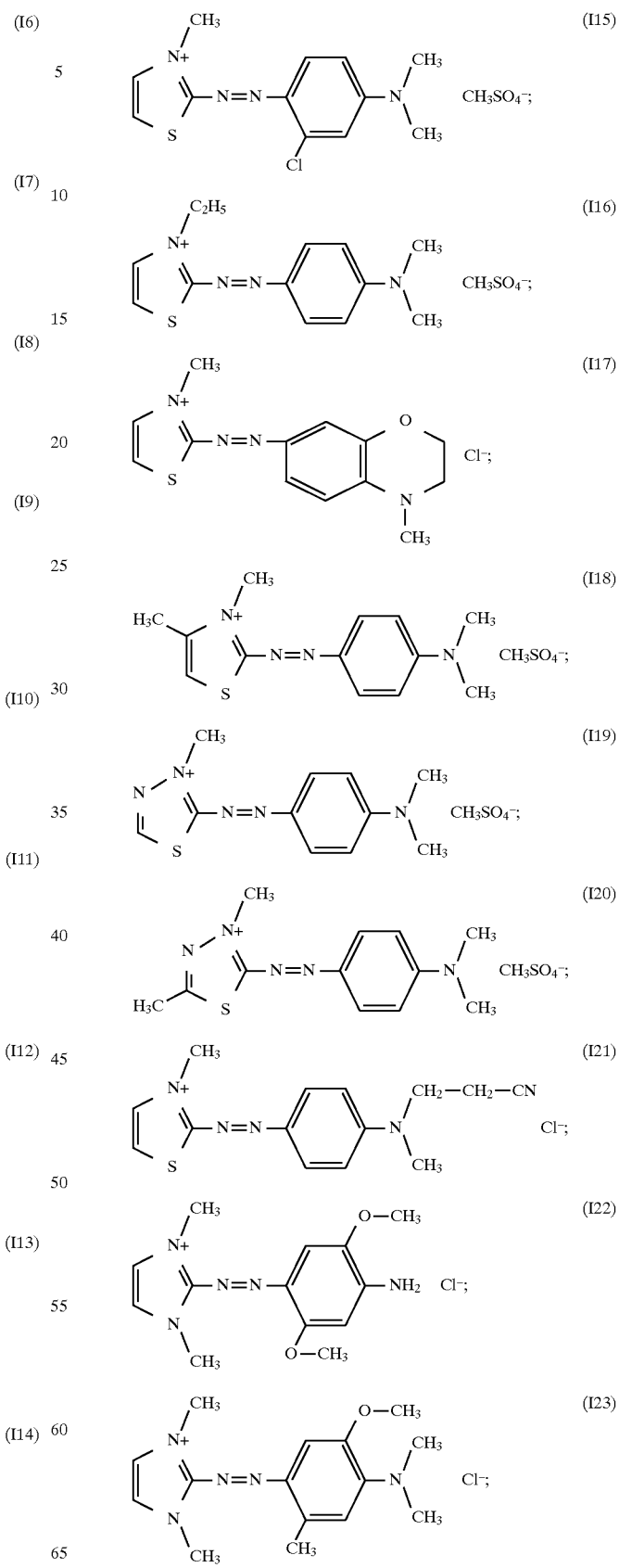

-continued

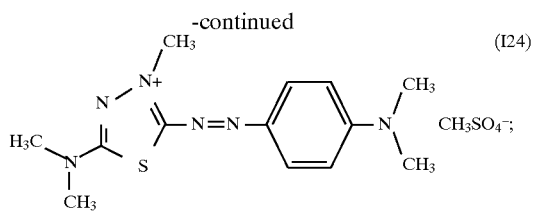

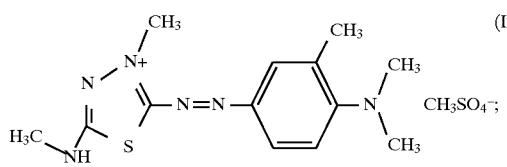

and

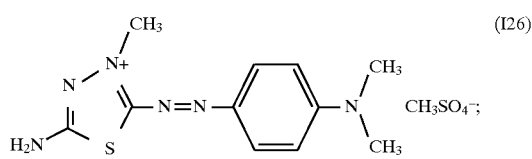

Among the specific compounds of structures (I1) to (I26) described above, the compound corresponding to structure (I1) is more particularly preferred.

The acid-addition salts which can be used in the context of the dye compositions of the invention are selected in particular from the hydrochlorides, hydrobromides, sulphates and tartrates.

The oxidizing agent present in the dye composition is selected from the oxidizing agents used conventionally in oxidation dyeing and preferably from hydrogen peroxide, urea peroxide, alkali metal bromates and persalts such as perborates and persulphates. Hydrogen peroxide is particularly preferred.

The cationic direct dye(s) of formula (I) in accordance with the invention preferably represent(s) from approximately 0.001 to approximately 10% by weight relative to the total weight of the ready-to-use dye composition, and even more preferably from approximately 0.05 to approximately 2% by weight relative to the total weight of the ready-to-use dye composition.

The oxidation base(s) in accordance with the invention, that is to say the para-phenylenediamine(s) preferably of formula (II) and/or the bis(phenyl)alkylenediamine(s) preferably of formula (III), preferably represent(s) from approximately 0.0001 to approximately 10% by weight relative to the total weight of the ready-to-use dye composition, and even more preferably from approximately 0.001 to approximately 5% by weight relative to the total weight of the ready-to-use dye composition.

The meta-phenylenediamine(s) preferably of formula (IV) in accordance with the invention preferably represent(s) from approximately 0.0001 to approximately 5% by weight relative to the total weight of the ready-to-use dye composition, and even more preferably from approximately 0.005 to approximately 3% by weight relative to the total weight of the ready-to-use dye composition.

The pH of the dye composition as defined above generally ranges from approximately 5 to approximately 12. It can be adjusted to the desired value using acidifying or basifying agents usually used in the dyeing of keratin fibers.

Among the acidifying agents, mention may be made, by way of example, of inorganic or organic acids such as hydrochloric acid, orthophosphoric acid, carboxylic acids such as tartaric acid, citric acid or lactic acid, and sulphonic acids.

Among the basifying agents, mention may be made, by way of example, of aqueous ammonia, alkaline carbonates, alkanolamines such as mono-, di- and triethanolamines and derivatives thereof, sodium hydroxide, potassium hydroxide and the compounds of formula (V) below:

in which:

R is a propylene residue optionally substituted with a hydroxyl group or a $C_1$–$C_4$ alkyl radical;

$R_{20}$, $R_{21}$, $R_{22}$ and $R_{23}$ each independently represents a hydrogen atom or a $C_1$–$C_4$ alkyl or $C_1$–$C_4$ hydroxyalkyl radical.

In addition to the dyes defined above, the dye composition in accordance with the invention can also contain other couplers and/or direct dyes, in particular in order to modify the shades or to enrich them with glints.

The suitable dyeing medium (or the support) for the ready-to-use dye composition in accordance with the invention generally comprises water or a mixture of water and at least one organic solvent in order to dissolve the compounds which would not be sufficiently soluble in water. By way of organic solvent, mention may be made, for example, of $C_1$–$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably ranging from approximately 1 to approximately 40% by weight relative to the total weight of the dye composition, and even more preferably from approximately 5 to approximately 30% by weight relative to the total weight of the dye composition.

The ready-to-use dye compositions in accordance with the invention can also contain various adjuvants used conventionally in compositions for dyeing the hair, such as anionic, cationic, nonionic or amphoteric surfactants or mixtures thereof, anionic, cationic, nonionic or amphoteric polymers or mixtures thereof, inorganic or organic thickeners, antioxidants, penetration agents, sequestering agents, fragrances, buffers, dispersing agents, packaging agents, film-forming agents, preserving agents and opacifiers.

Needless to say, a person skilled in the art will take care to select the optional additional compound(s) mentioned above such that the advantageous properties intrinsically associated with the ready-to-use dye composition in accordance with the invention are not, or are not substantially, adversely affected by the addition(s) envisaged.

The ready-to-use dye compositions in accordance with the invention can be in various forms, such as in the form of liquids, creams or gels or in any other form which is appropriate for dyeing keratin fibers, and in particular human hair.

A subject of the invention is also a process for dyeing keratin fibers, and in particular human keratin fibers such as the hair, using the ready-to-use dye composition as defined above.

According to this process, the ready-to-use dye composition as defined above is applied to the fibers and is left on them for an exposure time preferably of from approximately 3 to approximately 40 minutes, more preferably from approximately 5 to approximately 30 minutes, after which the fibers are rinsed, optionally washed with shampoo, rinsed again and dried.

According to a first preferred embodiment, the process includes a preliminary step which involves separately storing, on the one hand, a composition (A) comprising, in a medium which is suitable for dyeing, at least one oxidation base selected from para-phenylenediamines and bis(phenyl) alkylenediamines, and the acid-addition salts thereof, at least one coupler selected from meta-phenylenediamines and the acid-addition salts thereof, and at least one cationic direct dye selected from the compounds of formula (I), as defined above, and, on the other hand, a composition (B) containing, in a medium which is suitable for dyeing, at least one oxidizing agent as defined above, and mixing them together at the time of use before applying this mixture to the keratin fibers.

According to a second preferred embodiment, the process includes a preliminary step which involves separately storing, on the one hand, a composition (A) comprising, in a medium which is suitable for dyeing, at least one oxidation base selected from para-phenylenediamines and bis(phenyl) alkylenediamines, and the acid-addition salts thereof, at least one coupler selected from meta-phenylenediamines and the acid-addition salts thereof; on the other hand, a composition (A') comprising, in a medium which is suitable for dyeing, at least one cationic direct dye selected from the compounds of formula (I), as defined above; and, lastly, a composition (B) containing, in a medium which is suitable for dyeing, at least one oxidizing agent as defined above, and mixing them together at the time of use before applying this mixture to the keratin fibers.

The composition (A') used according to this second variant of the process in accordance with the invention can optionally be in powder form, the cationic direct dye(s) of formula (I) in accordance with the invention itself (themselves) constituting, in this case, all of the said composition (A') or optionally being dispersed in an organic and/or inorganic pulverulent excipient.

When it is present in the composition A', the organic excipient can be of synthetic or plant origin and is selected in particular from crosslinked and non-crosslinked synthetic polymers, polysaccharides such as celluloses and modified or unmodified starches, as well as natural products containing them such as sawdust and plant gums (guar gum, carob gum, xanthan gum, etc.).

When it is present in the composition (A'), the inorganic excipient can contain metal oxides such as titanium oxides, aluminium oxides, kaolin, talc, silicates, mica and silicas.

An advantageous excipient preferred according to the invention is sawdust.

The powdered composition (A') can also contain binders or coating products in an amount which preferably does not exceed approximately 3% by weight relative to the total weight of the said composition (A').

These binders are preferably selected from oils and liquid fatty substances of inorganic, synthetic, animal or plant origin.

The composition (A') may optionally also contain other adjuvants, in powdered form, in particular surfactants of any kind, hair conditioners such as, for example, cationic polymers, etc.

Another subject of the invention is a multi-compartment dyeing device or "kit" or any other multi-compartment packaging system, a first compartment which contains the composition (A) as defined above, an optional second compartment contains the composition (A') as defined above, when it is present, and a third compartment contains the oxidizing composition (B) as defined above. These devices can be equipped with means which allow the desired mixture to be applied to the hair, such as the devices described in French patent FR-2,586,913, the disclosure of which is specifically incorporated by reference herein.

The examples which follow are intended to illustrate the invention without, however, limiting its scope.

EXAMPLE 1

The following composition 1(A), in accordance with the invention, was prepared (contents in grams):

| COMPOSITION | 1 (A) | |
|---|---|---|
| Para-phenylenediamine | 0.7 | |
| 2,4-diamino-1-(β-hydroxyethyloxy)benzene dihydrochloride | 0.35 | |
| Cationic dye of structure (I1) | 0.4 | |
| Common dye support (*) | (*) | |
| Water qs | 100 g | |

| (*) Common dye support: | | |
|---|---|---|
| Oleyl alcohol polyglycerolated with 2 mol of glycerol | 4.0 | g |
| Oleyl alcohol polyglycerolated with 4 mol of glycerol, containing 78% active material (A.M.) | 5.69 | g A.M. |
| Oleic acid | 3.0 | g |
| Oleylamine containing 2 mol of ethylene oxide, sold under the trade name ETHOMEEN O12 by the company Akzo | 7.0 | g |
| Diethylaminopropyl laurylaminosuccinamate, sodium salt, containing 55% A.M. | 3.0 | g A.M. |
| Oleyl alcohol | 5.0 | g |
| Oleic acid diethanolamide | 12.0 | g |
| Propylene glycol | 3.5 | g |
| Ethyl alcohol | 7.0 | g |
| Dipropylene glycol | 0.5 | g |
| Propylene glycol monomethyl ether | 9.0 | g |
| Sodium metabisulphite as an aqueous solution containing 35% A.M. | 0.455 | g A.M. |
| Ammonium acetate | 0.8 | g |
| Antioxidant, sequestering agent | | qs |
| Fragrance, preserving agent | | qs |
| Aqueous ammonia containing 20% $NH_3$ | 10.0 | g |

Composition 1(A) was mixed, at the time of use, with an equal amount of a composition B comprising a 20-volumes hydrogen peroxide solution (6% by weight).

The resulting composition (ready-to-use composition in accordance with the invention) was applied for 30 minutes to locks of natural grey hair containing 90% white hairs. The hair was then rinsed, washed with a standard shampoo and then dried.

The hair was dyed a radiant ash-chestnut shade which effectively withstood subsequent shampooing.

According to a variant of the invention, the cationic direct dye of structure (I1) can be incorporated into composition 1(A) at the time of use.

EXAMPLE 2

Composition 2(A) below was prepared:

Para-toluylenediamine sulphate 1.25 g

2-Amino-4-N-(β-hydroxyethyl)amino-1-methoxybenzene dihydrochloride 0.35 g

Common dye support as described above for Example 1 (*)

Demineralized water qs 100 g

Composition 2(A') below was prepared:

Cationic dye of structure (I1) 4 g

Quaternary polyammonium sold under the trade name CELQUAT SC-240 by the company National Starch 10 g Sawdust qs 100 g One part by weight of composition 2(A) above was mixed, at the time of use, with 0.1 part by weight of composition 2(A') and with one part by weight of a composition (B) comprising a 20-volumes hydrogen peroxide solution (6% by weight).

The resulting composition was applied for 30 minutes to locks of natural grey hair containing 90% white hairs. The hair was then rinsed, washed with a standard shampoo and then dried.

The hair was dyed in an ash-chestnut shade which effectively withstood subsequent shampooing.

We claim:

1. A ready-to-use composition for the oxidation dyeing of keratin fibers comprising, in a medium suitable for dyeing:

at least one oxidation base selected from para-phenylenediamines or bis(phenyl)alkylenediamines, or the acid-addition salts thereof, at least one coupler selected from meta-phenylenediamines, or the acid-addition salts thereof, at least one cationic direct dye selected from the compounds of formula (I) below:

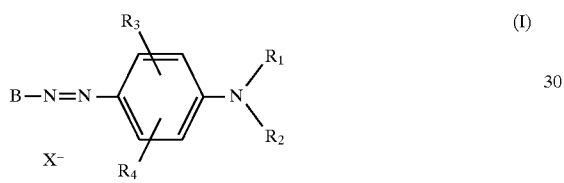

in which:

$R_1$ represents a hydrogen atom, or a $C_1$–$C_4$ alkyl radical, $R_2$ represents a hydrogen atom, an alkyl radical which may be substituted with a —CN radical or with an amino group, a 4'-aminophenyl radical or forms, with $R_1$ or with a carbon atom of the benzene ring supporting the radicals $R_3$ and $R_4$, an optionally oxygenated and/or nitrogenous heterocycle which may be substituted with a $C_1$–$C_4$ alkyl radical, $R_3$ and $R_4$ each independently represents a hydrogen atom, a halogen atom, a $C_1$–$C_4$ alkyl or $C_1$–$C_4$ alkoxy radical or a —CN radical, $X^-$ represents an anion selected from chloride, methylsulphate or acetate, B represents a group selected from the structures B1 to B11:

in which:

$R_5$ represents a $C_1$–$C_4$ alkyl radical, $R_6$ and $R_7$ each independently represent a hydrogen atom or a $C_1$–$C_4$ alkyl radical;

wherein when $R_1$ and $R_2$ form a nitrogenous heterocycle, or when $R_3$ and $R_4$ represent a $C_1$–$C_4$ alkyl radical or a $C_1$–$C_4$ alkoxy radical, or when $R_2$ represents a 4'-aminophenyl radical, then B may also be selected from a group of structure B12:

in which:

$R_5$ represents a $C_1$–$C_4$ alkyl radical; and at least one oxidizing agent.

2. A ready-to-use composition according to claim 1, wherein said keratin fibers are human hair.

3. A ready-to-use composition according to claim 1, wherein with respect to $R_3$ and $R_4$, said halogen atom is selected from bromine, chlorine, iodine or fluorine.

4. A ready-to-use composition according to claim 1, wherein said para-phenylenediamines are selected from compounds of formula (II) or the acid-addition salts thereof:

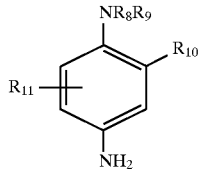

(II)

in which:
- $R_8$ represents a hydrogen atom, a $C_1$–$C_4$ alkyl, $C_1$–$C_4$ monohydroxyalkyl, $C_2$–$C_4$ polyhydroxyalkyl, phenyl, 4'-aminophenyl or ($C_1$–$C_4$)alkoxy($C_1$–$C_4$)alkyl radical,
- $R_9$ represents a hydrogen atom or a $C_1$–$C_4$ alkyl, $C_1$–$C_4$ monohydroxyalkyl or $C_2$–$C_4$ polyhydroxyalkyl radical,
- $R_{10}$ represents a hydrogen atom, a halogen atom, a $C_1$–$C_4$ alkyl, $C_1$–$C_4$ monohydroxyalkyl, $C_1$–$C_4$ hydroxyalkoxy, $C_1$–$C_4$ mesylaminoalkoxy, $C_1$–$C_4$ carbamoylaminoalkoxy or $C_1$–$C_4$ acetylaminoalkoxy radical,
- $R_{11}$ represents a hydrogen atom or a $C_1$–$C_4$ alkyl radical.

5. A ready-to-use composition according to claim 4, wherein with respect to $R_{10}$, said halogen atom is selected from chlorine, bromine, iodine or fluorine.

6. A ready-to-use composition according to claim 5, wherein said para-phenylenediamines of formula (II) are selected from:
para-phenylenediamine,
para-toluylenediamine,
2-chloro-para-phenylenediamine,
2,3-dimethyl-para-phenylenediamine,
2,6-dimethyl-para-phenylenediamine,
2,6-diethyl-para-phenylenediamine,
2,5-dimethyl-para-phenylenediamine,
N,N-dimethyl-para-phenylenediamine,
N,N-diethyl-para-phenylenediamine,
N,N-dipropyl-para-phenylenediamine,
4-amino-N,N-diethyl-3-methylaniline,
N,N-bis(β-hydroxyethyl)-para-phenylenediamine,
4-amino-N,N-bis(β-hydroxyethyl)-3-methylaniline,
4-amino-3-chloro-N,N-bis(β-hydroxyethyl)aniline,
2-β-hydroxyethyl-para-phenylenediamine,
2-fluoro-para-phenylenediamine,
2-isopropyl-para-phenylenediamine,
N-(β-hydroxypropyl)-para-phenylenediamine,
2-hydroxymethyl-para-phenylenediamine,
N,N-dimethyl-3-methyl-para-phenylenediamine,
N,N-(ethyl-β-hydroxyethyl)-para-phenylenediamine,
N-(β,γ-dihydroxypropyl)-para-phenylenediamine,
N-(4'-aminophenyl)-para-phenylenediamine,
N-phenyl-para-phenylenediamine,
2-β-hydroxyethyloxy-para-phenylenediamine,
2-β-acetylaminoethyloxy-para-phenylenediamine,
or the acid-addition salts thereof.

7. A ready-to-use composition according to claim 6, wherein said said para-phenylenediamine of formula (II) are selected from:
para-phenylenediamine,
para-toluylenediamine,
2-chloro-para-phenylenediamine,
2,3-dimethyl-para-phenylenediamine,
2,6-dimethyl-para-phenylenediamine,
2,6-diethyl-para-phenylenediamine,
N,N-bis(β-hydroxyethyl)-para-phenylenediamine,
2-β-hydroxyethyl-para-phenylenediamine,
2-isopropyl-para-phenylenediamine,
2-β-hydroxyethyloxy-para-phenylenediamine,
or the acid-addition salts thereof.

8. A ready-to-use composition according to claim 1, wherein said bis(phenyl)alkylenediamines are selected from compounds of formula (III), or the acid-addition salts thereof:

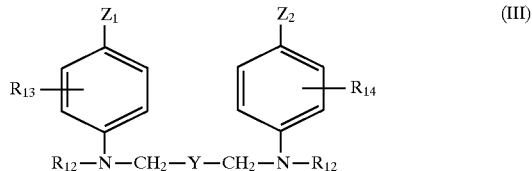

(III)

in which:
- $Z_1$ and $Z_2$ each independently represents a hydroxyl radical or $NHR_{15}$ in which
- $R_{15}$ represents a hydrogen atom or a $C_1$–$C_4$ alkyl radical,
- $R_{12}$ represents a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino portion of said aminoalkyl radical can be substituted,
- $R_{13}$ and $R_{14}$ each independently represents a hydrogen or halogen atom or a $C_1$–$C_4$ alkyl radical,
- Y represents a radical selected from the following radicals:

$-(CH_2)_n-$; $-(CH_2)_m-O-(CH_2)_m-$; $-(CH_2)m-CHOH-(CH_2)_m-$ or

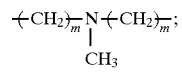

in which
n is an integer ranging from 0 to 8 and m is an integer ranging from 0 to 4.

9. A ready-to-use composition according to claim 8, wherein said bis(phenyl)alkylenediamines of formula (III) are selected from:
N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine,
N,N'-bis(4-aminophenyl)-tetramethylenediamine,
N,N'-bis(β-hydroxyethyl)-N,N'-bis(4-aminophenyl)tetramethylenediamine, N,N'-bis(4-methylaminophenyl)tetramethylenediamine,
N,N'-bis(ethyl)-N,N'-bis(4'-amino-3'-methylphenyl)ethylenediamine,
or the acid-addition salts thereof.

10. A ready-to-use composition according to claim 9, wherein said bis(phenyl)alkylenediamines of formula (III) are selected from N,N'-bis(β-hydroxyethyl)-N,N'-bis(4'-aminophenyl)-1,3-diaminopropanol or the acid-addition salts thereof.

11. A ready-to-use composition according to claim 1, wherein said meta-phenylenediamines are selected from compounds of formula (IV), or the acid-addition salts thereof:

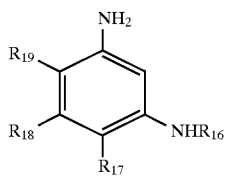

in which:

R$_{16}$ represents a hydrogen atom or a C$_1$–C$_4$ alkyl, C$_1$–C$_4$ monohydroxyalkyl or C$_2$–C$_4$ polyhydroxyalkyl radical;

R$_{17}$ and R$_{18}$ each independently represents a hydrogen atom or a C$_1$–C$_4$ alkyl, C$_1$–C$_4$ monohydroxyalkoxy or C$_2$–C$_4$ polyhydroxyalkoxy radical;

R$_{19}$ represents a hydrogen atom, a C$_1$–C$_4$ alkoxy, C$_1$–C$_4$ aminoalkoxy, C$_1$–C$_4$ monohydroxyalkoxy or C$_2$–C$_4$ polyhydroxyalkoxy radical or a 2,4-diaminophenoxyalkoxy radical.

12. A ready-to-use composition according to claim 11, wherein said meta-phenylenediamines of formula (IV) are selected from:
meta-phenylenediamine,
3,5-diamino-1-ethyl-2-methoxybenzene,
3,5-diamino-2-methoxy-1-methylbenzene,
2,4-diamino-1-ethoxybenzene,
1,3-bis(2,4-diaminophenoxy)propane,
bis(2,4-diaminophenoxy)methane,
1-(β-aminoethyloxy)-2,4-diaminobenzene,
2-amino-1-(β-hydroxyethyloxy)-4-methylaminobenzene,
2,4-diamino-1-ethoxy-5-methylbenzene,
2,4-diamino-5-(β-hydroxyethyloxy)-1-methylbenzene,
2,4-diamino-1-(β,γ-dihydroxypropyloxy)benzene,
2,4-diamino-1-(β-hydroxyethyloxy)benzene,
2-amino-4-N-(β-hydroxyethyl)amino-1-methoxybenzene,
or the acid-addition salts thereof.

13. A ready-to-use composition according to claim 1, wherein said at least one cationic direct dye of formula (I) is selected from compounds corresponding to structures (I1) to (I26):

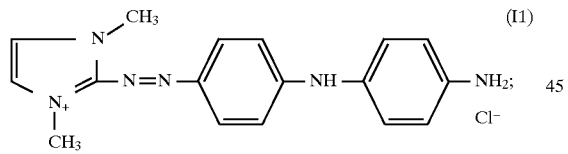

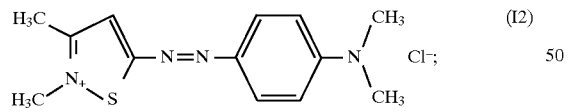

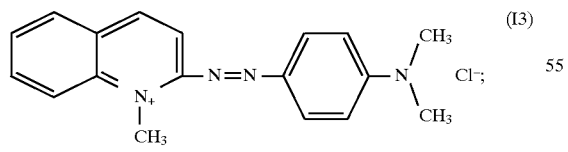

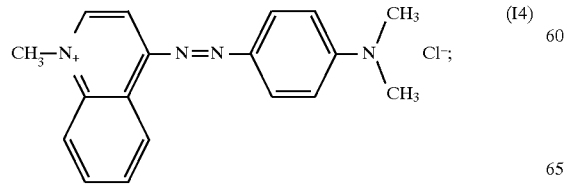

-continued

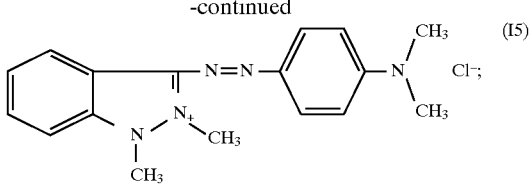

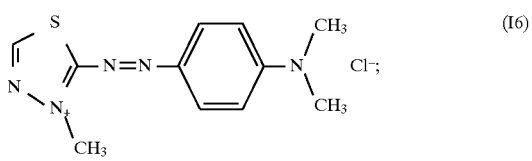

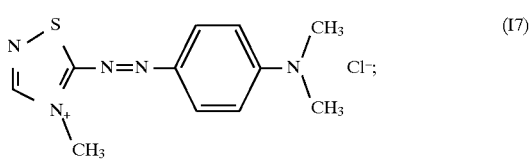

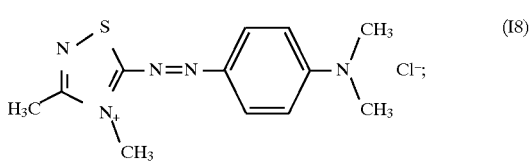

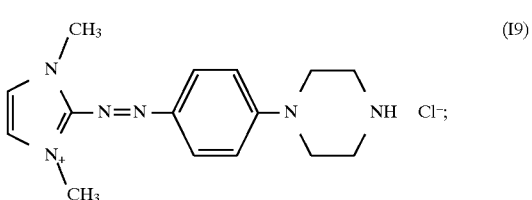

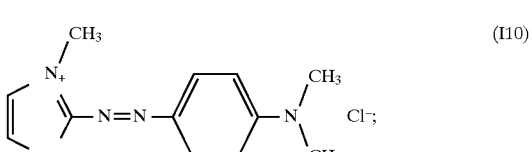

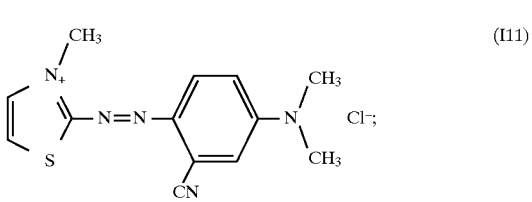

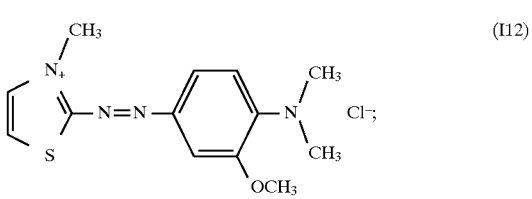

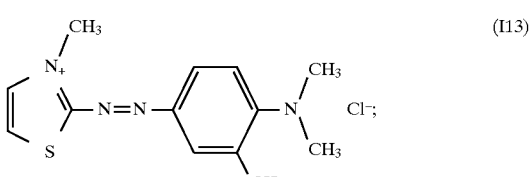

-continued

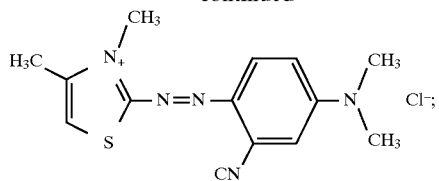 (I14)

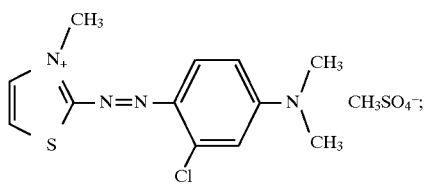 (I15)

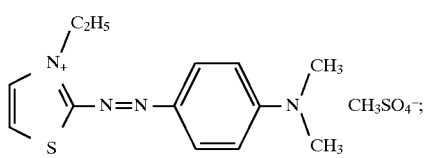 (I16)

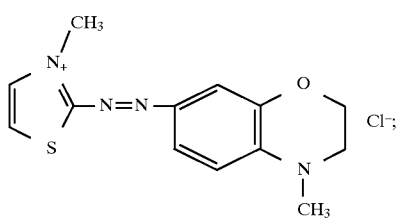 (I17)

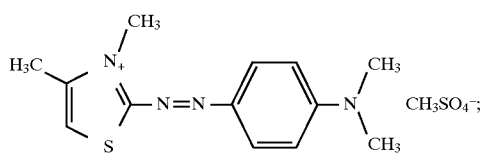 (I18)

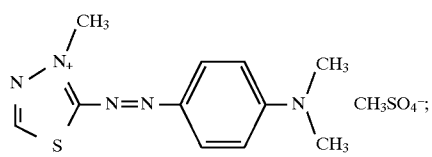 (I19)

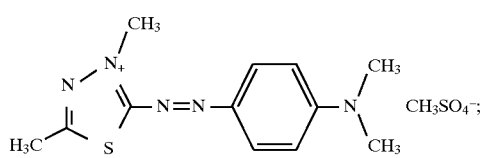 (I20)

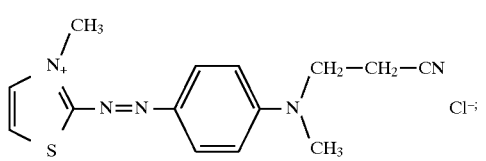 (I21)

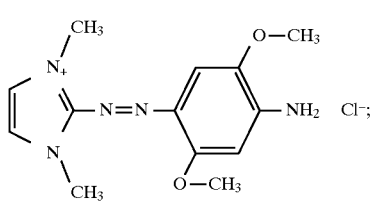 (I22)

-continued

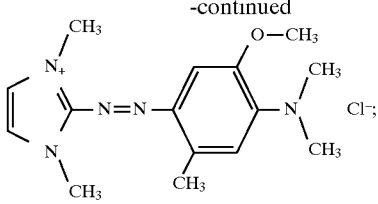 (I23)

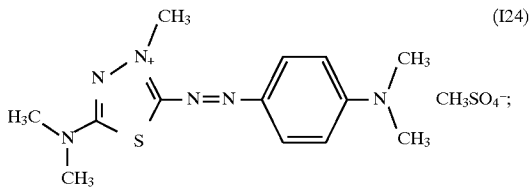 (I24)

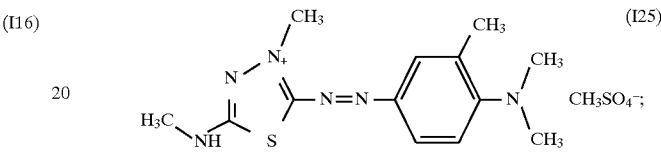 (I25)

or

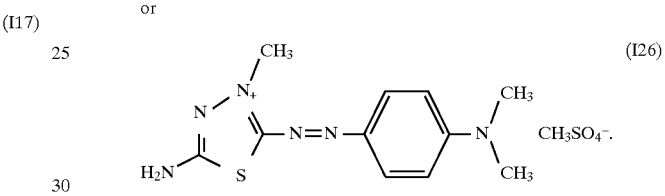 (I26)

14. A ready-to-use composition according to claim 13, wherein said at least one cationic direct dye of formula (I) is a compound corresponding to structure (I1).

15. A ready-to-use composition according to claim 1, wherein said acid-addition salts are selected from hydrochlorides, hydrobromides, sulphates or tartrates.

16. A ready-to-use composition according to claim 1, wherein said at least one oxidizing agent is selected from hydrogen peroxide, urea peroxide, alkali metal bromates or persalts.

17. A ready-to-use composition according to claim 16, wherein said persalts are selected from perborates or persulphates.

18. A ready-to-use composition according to claim 16, wherein said at least one oxidizing agent is hydrogen peroxide.

19. A ready-to-use composition according to claim 1, wherein said at least one cationic direct dye of formula (I) is present in a concentration ranging from 0.001 to 10% by weight relative to the total weight of the ready-to-use dye composition.

20. A ready-to-use composition according to claim 1, wherein said at least one oxidation base is present in a concentration ranging from 0.0001 to 10% by weight relative to the total weight of the ready-to-use dye composition.

21. A ready-to-use composition according to claim 1, wherein said at least one coupler is present in a concentration ranging from 0.0001 to 5% by weight relative to the total weight of the ready-to-use dye composition.

22. A ready-to-use composition according to claim 1, wherein said composition has a pH ranging from 5 to 12.

23. A ready-to-use composition according to claim 1, wherein said medium suitable for dyeing comprises water or a mixture of water and at least one organic solvent.

24. A ready-to-use composition according to claim 1, wherein said ready-to-use composition is in the form of a liquid, a cream, a gel, or any form suitable for dyeing keratin fibers.

25. A process for dyeing keratin fibers comprising applying at least one ready-to-use composition according to claim 1 to said fibers.

26. A process according to claim 25, wherein said keratin fibers are human hair.

27. A process for dyeing keratin fibers according to claim 25, wherein said ready-to-use dye composition is left on said keratin fibers for a time ranging from 3 to 40 minutes, and then is rinsed, optionally washed with shampoo, rinsed again and dried.

28. A process for dyeing keratin fibers according to claim 27, wherein said ready-to-use dye composition is left on said keratin fibers for a time ranging from 5 to 30 minutes.

29. A process for dyeing keratin fibers comprising:
  applying at least one ready-to-use composition according to claim 1 to said keratin fibers, wherein said process further comprises the preliminary steps of:
  preparing a composition (A) comprising, in a medium which is suitable for dyeing, at least one oxidation base according to claim 1, at least one coupler according to claim 1, and at least one cationic direct dye according to claim 1,
  separately preparing a composition (B) comprising, in a medium which is suitable for dyeing, at least one oxidizing agent according to claim 1,
  separately storing composition (A) from composition (B), and
  mixing said composition (A) and said composition (B) together immediately before applying to said keratin fibers.

30. A process for dyeing keratin fibers comprising applying at least one ready-to-use composition according to claim 1 to said keratin fibers, wherein said process further comprises the preliminary steps of:
  preparing a composition (A) comprising, in a medium which is suitable for dyeing, at least one oxidation base according to claim 1 and at least one coupler according to claim 1,
  separately preparing a composition (A') comprising, in a medium which is suitable for dyeing, at least one cationic direct dye according to claim 1,
  separately preparing a composition (B) comprising, in a medium which is suitable for dyeing, at least one oxidizing agent according to claim 1, and
  mixing said composition (A), said composition (A'), and said composition (B) together immediately before applying to said keratin fibers.

31. A process according to claim 30, wherein said composition (A') is powder form.

32. A multi-compartment dyeing device or kit, comprising a first compartment containing a composition (A) comprising, in a medium which is suitable for dyeing, at least one oxidation base according to claim 1, at least one coupler according to claim 1, and at least one cationic direct dye according to claim 1, and a second compartment containing an oxidizing composition (B) comprising, in a medium which is suitable for dyeing, at least one oxidizing agent according to claim 1.

33. A multi-compartment dyeing device or kit, comprising a first compartment containing a composition (A) comprising, in a medium which is suitable for dyeing, at least one oxidation base according to claim 1 and at least one coupler according to claim 1, a second compartment contains a composition (A') comprising, in a medium which is suitable for dyeing, at least one cationic direct dye according to claim 1, and a third compartment containing an oxidizing composition (B) comprising, in a medium which is suitable for dyeing, at least one oxidizing agent according to claim 1.

* * * * *